United States Patent [19]

Hancock

[11] Patent Number: 5,308,870
[45] Date of Patent: May 3, 1994

[54] RACTOPAMINE FOR PRE-AND PERIPUBERTAL FEMALE BOVIDAE

[75] Inventor: Deana L. Hancock, Lafayette, Ind.

[73] Assignee: Eli Lilly and Company, Indianapolis, Ind.

[21] Appl. No.: 994,034

[22] Filed: Dec. 21, 1992

[51] Int. Cl.⁵ ............................................. A61K 31/135
[52] U.S. Cl. .................................................... 514/653
[58] Field of Search ................................ 514/650, 653

[56] References Cited

U.S. PATENT DOCUMENTS 4,690,951 9/1987 Anderson et al. ................. 514/653
4,904,662 2/1990 Anderson et al. ............... 514/237.8

FOREIGN PATENT DOCUMENTS

67/3994 3/1967 South Africa .

OTHER PUBLICATIONS

*Acta. Agr. Scand.*, 28, 41–46 (1978).
*J. Dairy Sci.*, 43, 377–387 (1960).
*J. Dairy Sci.*, 65, 793–800 (1982).
*Feedstuffs*, Apr. 6, 1992, 12, 13, and 17.
*Korean J. An. Sci.*, 32(9), 547–553 (1990) and translation.
*J. Nutr. Biochem.*, 3, #1, 2–7 (1992).
*J. An. Sci.*, 68, Supp. #1, 284 (1990).
*J. An. Sci.*, 69, Supp. #1, 332 (1991).
*J. An. Sci.*, 67, Supp. #1, 190–191 (1989).
*Protoplasma*, 159, #2-3, 96–111 (1990).
*Recueil*, 92, 1281–1297 (1973).

*Primary Examiner*—Frederick E. Waddell
*Assistant Examiner*—Kevin E. Weddington
*Attorney, Agent, or Firm*—Kathleen R. S. Page; Leroy Whitaker

[57] ABSTRACT

The present invention is directed to a method for increasing the milk producing capacity of a female bovidae, by administering an effective amount of an active agent to the bovidae during its mammary glands' allometric growth phase preceding first conception. The active agent is ractopamine or a physiologically acceptable salt.

5 Claims, No Drawings

RACTOPAMINE FOR PRE-AND PERIPUBERTAL FEMALE BOVIDAE

BRIEF SUMMARY OF THE INVENTION

The rearing of female bovidae, in a manner to maximize their milk production, is a matter which has received a great deal of attention. This is because the parenchyma, the functional milk-secreting portion of the mammary glands, is to a substantial degree developed prior to puberty. Studies have been undertaken to enhance parenchymal development. Surprisingly, increased feed consumption in the prepubertal period, while it may lead to increased growth rate and earlier puberty, results in decreased milk production.

There has now been discovered a method by which pre- and peripubertal female bovidae can be treated, with the result that parenchymal tissue is increased and the ultimate milk producing capacity of the animal increased. This method is the administration of an active agent which is 1-(4-hydroxyphenyl)-2-(1-methyl-3-(4-hydroxyphenyl)propylamino)ethanol, or a physiologically acceptable salt thereof.

DETAILED DESCRIPTION OF THE INVENTION

The active agent to be employed in the present method is 1-(4-hydroxyphenyl)-2-(1-methyl-3-(4-hydroxyphenyl)propylamino)ethanol, or a physiologically acceptable salt thereof. The compound has the following formula:

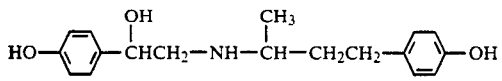

It is known by its USAN name of "ractopamine." It has two asymmetric carbon atoms. In the present invention, an individual isomer can be used, but preferably the compound is employed as a mixture of the isomers. The hydrochloride is the preferred salt.

The compounds to be used in the present invention are the subject of U.S. Pat. No. 4,690,951, which is incorporated herein by reference.

The development of the mammary gland is a complex process. A good review is presented in the Apr. 6, 1992, issue of Feedstuffs, pages 12, 13, and 17. In summary, from shortly after birth until somewhat after puberty, the growth of the mammary glands occurs at an "allometric" rate, that is, at a rate greater than the general growth rate of the animal ("isometric"). See Acta. Agr. Scand., 28, 41–46 (1978). During this allometric growth phase, growth is directed to both the parenchymal tissue, the ductular epithelial tissue on which actual milk secretary tissue will later form, as well as to the fat pad in which the parenchyma is embedded. Subsequent milk production is maximized by increasing the growth of the parenchyma and minimizing the growth of the fat pad during this allometric growth phase.

Higher milk production is desirable for those breeds that are used for dairy purposes, since the milk is sold. Higher milk production is also desirable for those breeds in which the practice is to allow the offspring to suckle. The offspring has a larger supply of milk for sustenance, and achieves a higher weight by weaning.

In the present invention, the active agent is administered to a female bovidae during its mammary glands' allometric growth phase preceding first conception.

The age at which each species reaches puberty and can be bred is known. Females from Bos taurus generally reach puberty when they are two-thirds of "adult" size for the particular breed. This will occur in a period ranging from 4 months to 14 months of age. In sheep and goats, puberty is only in part controlled by size, being also controlled by seasonality; in general, these species reach puberty at 40 to 70 percent of their adult size, which is generally attained at 5 to 10 months. However, cycling may be delayed for a year if the necessary size is reached late in autumn. Buffaloes reach puberty at 1 to 3 years of age. In addition to these species differences, there are additional variations among particular breeds and also depending on the management practices used. The attainment of puberty by any individual animal can be determined by observation for behavioral signs of estrus, or by methods known to those skilled in the science of animal management, notably by analysis of blood samples for progesterone.

In the preferred practice, the present active agent is administered in the latter portion of the allometric growth phase, which will include the period prior to puberty (first estrus) and may include the early post puberty period. However, around puberty, the allometric growth phase is gradually converted to an isometric phase, and the opportunity for beneficially altering the development of the mammary glands is reduced. Therefore, in a particularly preferred practice, the present active agent is administered in the period prior to puberty. The length of this period will vary with the particular bovidae to be treated. In bovidae which are Bos taurus, the period will generally be two to four months preceding puberty.

Among the Bos genera, the present invention can be practiced with dairy breeds such as the Holstein, Jersey, Guernsey, Brown Swiss, Ayrshire, Friesian, Dutch Red and White, Danish Red, and Normande. The present invention can be practiced with beef breeds such as the Angus, Hereford, Chianina, Penzgauer, Red Angus, Polled Hereford, Devon, South Devon, Santa Gertrudis, Galloway, Maine-Anjou, Brangus, Brahman, Gelbvieh, Charolais, and Limousin, as well as crossbreds. Additionally, some breeds, such as the Simmental and Shorthorn, are used for both dairy and beef purposes. The present invention can also be practiced on other female bovidae, such as goats, sheep, and buffaloes.

The present active agent can be administered in any of a number of ways. The compound can be administered orally, as part of a complete feed, as a topdress, as a supplement, or in drinking water. The compound can be combined with a physiologically acceptable carrier and injected into the animal to be treated. The compound can be formulated as part of an implant, which is inserted subcutaneously and from which the active agent is delivered over a period of time. The most preferred manner of delivery is orally, in the feed. For such purposes, an effective amount of the active agent can be delivered in feeds containing the present active agent in a concentration of from 5 to 200 ppm, and preferably from 20 to 125 ppm.

The present invention is exemplified by the following example. Forty prepubertal Holstein heifers were used in this experiment. Average weight and age at the beginning of the study were approximately 249 kg and 244 days (8 months). Heifers were paired according to weight and age and assigned to either a control or experimental treatment. Heifers were maintained in pens of four. The experimental treatment was ractopamine fed at 80 ppm of the diet on a dry matter basis. Duration of the treatment was 70 days.

Heifers were fed ad libitum each day a complete mixed ration (% of total on a DM basis) consisting of corn silage (21.1%), alfalfa silage (15%), and supplement (60%) as a complete mixed ration plus topdress (3.9%). Composition of the supplement (CA-95) and topdress (DA-74) is shown in Table 1A. A premix containing ractopamine (composition, Table 1B) was mixed with sufficient DA-74 to provide 184.7 mg ractopamine per kg of topdress. An identical topdress without ractopamine was fed to control heifers. The amount of topdress was such as to provide 80 ppm of ractopamine, based on the entire diet. The mixed diet was offered once daily. Immediately prior to feeding, the amount of feed refusal from the previous day's feeding was determined. The required amount of topdress was added to the fresh feed and mixed in the feed bunk immediately after feeding.

Body weight of heifers was determined beginning on the first day of the study and continuing at seven day intervals throughout the 70 d treatment period. Body weights at the beginning and end of the study were the average of two consecutive day weighings. Height at the withers was determined at the beginning and end of the study.

At the end of the study, heifers were euthanized and the mammary gland and ovaries removed. Mammary glands were trimmed, removing medial and lateral suspensory ligaments and excess skin. Trimmed glands were weighed and dissected. The skin and teats were removed first. Next, extraneous tissue (mostly fascia) was removed from the dorsal surface of the gland. The remainder of the nonmammary tissue was separated physically from the anterior and lateral portions of the gland and fat pad. The supra mammary lymph nodes were removed as well. The gland was then separated into left and right halves and weighed.

The right half of the mammary gland from 36 heifers was dissected into parenchymal and nonparenchymal tissue. Each component was weighed and tissue portions submitted for analysis of water by oven drying at 100 C. for 24 hr and of lipid by ether extract, and of protein by Kjeldahl.

Results

Animal performance is shown in Table 2. Gain was increased (P<0.07) by 0.13 kg/d in heifers fed ractopamine. The difference in ADG diminished as time on treatment increased. Differences in ADG between control and treated heifers after 28, 42 and 56 days of treatment were 0.35, 0.20, and 0.17 kg/d, respectively. Dry matter intake between treatments was similar such that feed required per kg of gain was decreased (P<0.06) by 8.3%. There was no difference between treatments in hot carcass weight or dressing percentage.

Weight of the mammary gland and its tissue types are shown in Table 3. The total weight of mammary glands from control heifers was 7.9% greater than for heifers fed ractopamine. The difference between treatments in trimmed weight of the mammary glands was not statistically significant. Likewise, differences between treatments for actual weight of each tissue type and proportion of tissue type as a percent of the total gland were not statistically significant. However, the mammary glands from heifers fed ractopamine weighed slightly less (4.7%) than the glands from control heifers but contained slightly more parenchyma (3.1%) and less nonparenchyma (11.8%).

The tissue types once separated were analyzed for protein, lipid, ash and water content (Table 4). Parenchyma from mammary glands of heifers fed ractopamine contained a lower percentage of lipid (P<0.01) and an increased percentage of protein (P<0.06), water (P<0.01), and ash (P<0.01) when compared to mammary glands from control heifers. While there was a 11.8% reduction (P>0.2) in weight of nonparenchymal tissue in the mammary glands of heifers fed ractopamine, there were no differences in the chemical composition of the nonparenchymal tissue.

Actual weight of protein, lipid, ash and water in parenchymal and nonparenchymal tissues from mammary glands of heifers is shown in Table 5. There were no statistically significant differences between treatments for any chemical component of either parenchymal or nonparenchymal tissues.

The percentage and weight of protein, lipid, ash and water in the total gland are shown in Table 6. Mammary glands from heifers fed ractopamine contained on a percentage basis, higher protein (P<0.07) and water (P<0.03) and lower lipid (P<0.04). Feeding of ractopamine reduced (P<0.03) the weight of total lipid in the mammary gland but the effects of ractopamine on protein, ash, and water were not statistically significant.

In summary, although ractopamine-fed heifers gained (9.0%) more than control heifers (1.55 vs. 1.42 kg/d), parenchyma from mammary glands of ractopamine-fed heifers contained less (P<0.01) lipid and more (P<0.06) protein on a percentage basis than did control heifers. There was no effect of ractopamine on lipid content of the nonparenchymal tissue. These data indicate that ractopamine is useful in feeding pre- and peripubertal heifers for a higher rate of gain without the usual increase in lipid deposition in the developing mammary gland that normally occurs with such increases in gain.

TABLE 1A

| Composition (%) of supplement (CA-95) and topdress (DA-74). | | |
|---|---|---|
| Ingredient | CA-95 | DA-74 |
| Ground corn, yellow | 63.0 | 20.0 |
| Soybean meal (solvent extracted) | 10.0 | 25.0 |
| Cane molasses | 10.0 | 2.5 |
| Distillers dried grains | 9.0 | — |
| Corn cobs | — | 38.0 |
| Meat meal | 4.6 | — |
| Oats, ground | — | 11.0 |
| Animal fat | — | 2.0 |
| Mineral/vitamins | 2.8 | 1.1 |
| Salt | 0.6 | 0.4 |

TABLE 1B

| Composition of Premix Containing Ractopamine. | | |
|---|---|---|
| | % Ingredient | |
| | Ractopamine hydrochloride | Ground corn cobs |
| Lot #1 | 10 | 90 |
| Lot #2 | 5 | 95 |

TABLE 2

| Growth Performance. | | | | |
|---|---|---|---|---|
| | Control | Ractopamine | (Percent Change from Control) | P< |
| Gain, kg/d | 1.42 | 1.55 | (+9.2) | 0.07 |
| Feed/gain | 6.83 | 6.26 | (−8.3) | 0.06 |
| Dry matter | 9.7 | 9.6 | (−1.0) | 0.87 |

TABLE 2-continued

Growth Performance.

| | Control | Ractop-amine | (Percent Change from Control) | P< |
|---|---|---|---|---|
| intake, kg/d | | | | |
| Hot carcass, kg | 188.6 | 193.9 | (+2.8) | 0.18 |
| Dressing Pct | 54.2 | 54 | (−0.4) | 0.77 |

TABLE 3

Weight of mammary gland and of parenchyma and fat in mammary gland.

| | Control | Ractop-amine | (Percent Change from Control) | P< |
|---|---|---|---|---|
| Total weight, g | 3508 | 3231 | (−7.9) | 0.14 |
| Trimmed weight, g | 2285 | 2177 | (−4.7) | 0.39 |
| Mammary gland, % of Body Wt | 0.66 | 0.61 | (−7.6) | 0.19 |
| Right mammary gland weight, g | 1134.75 | 1082.1 | (−4.6) | 0.39 |
| Parenchyma, g | 554 | 571 | (+3.1) | 0.8 |
| Nonparenchyma, g | 574.7 | 506.9 | (−11.8) | 0.22 |
| Parenchyma, % of Mammary gland | 48.6 | 52.9 | (+8.8) | 0.31 |
| Nonparenchyma, % of Mammary gland | 50.9 | 47.1 | (−7.5) | 0.39 |

TABLE 4

Chemical composition of parenchymal and nonparenchymal tissues from mammary glands.

| | Control | Ractop-amine | (Percent Change from Control) | P< |
|---|---|---|---|---|
| Parenchyma, g | 554 | 571 | (+3.1) | 0.8 |
| Parenchyma, % lipid | 54.5 | 47.8 | (−12.3) | 0.01 |
| Parenchyma, % protein | 6.46 | 6.99 | (+8.2) | 0.06 |
| Parenchyma, % moisture | 37.9 | 43.7 | (+15.3) | 0.01 |
| Parenchyma, % ash | 0.43 | 0.52 | (+20.9) | 0.01 |
| Nonparenchyma, g | 574.7 | 506.9 | (−11.8) | 0.22 |
| Nonparenchyma, % lipid | 80.4 | 79.1 | (−1.6) | 0.28 |
| Nonparenchyma, % protein | 2.64 | 2.59 | (−1.9) | 0.8 |
| Nonparenchyma, % moisture | 16.1 | 17.5 | (+8.7) | 0.27 |
| Nonparenchyma, % ash | 0.15 | 0.11 | (−26.7) | 0.42 |

TABLE 5

Weight of chemical components in parenchymal and nonparenchymal tissues from mammary glands.

| | Control | Ractop-amine | (Percent Change from Control) | P< |
|---|---|---|---|---|
| Parenchyma, g | 554 | 571 | (+3.1) | 0.8 |
| Parenchyma, g of protein | 36 | 40.2 | (+11.7) | 0.38 |
| Parenchyma, g of lipid | 302.4 | 272.3 | (−10.0) | 0.26 |
| Parenchyma, g of water | 209.4 | 249.4 | (+19.1) | 0.26 |
| Parenchyma, g of ash | 2.4 | 3.0 | (+25.0) | 0.19 |
| Nonparenchyma, g | 574.7 | 506.9 | (−11.8) | 0.22 |
| Nonparenchyma, g of protein | 14.8 | 12.8 | (−13.5) | 0.41 |
| Nonparenchyma, g of lipid | 461.5 | 401 | (−13.1) | 0.15 |
| Nonparenchyma, g of water | 93.2 | 88.9 | (−4.6) | 0.73 |
| Nonparenchyma, g of ash | 0.9 | 0.6 | (−33.3) | 0.34 |

TABLE 6

Percentage and weight of chemical components from mammary glands.

| | Control | Ractop-amine | (Percent Change from Control) | P< |
|---|---|---|---|---|
| Total Gland, % | | | | |
| Protein | 4.47 | 4.93 | (+10.3) | 0.07 |
| Lipid | 67.5 | 62.5 | (−7.4) | 0.04 |
| Water | 26.5 | 31.4 | (+18.5) | 0.03 |
| Ash | 0.29 | 0.33 | (+13.8) | 0.38 |
| Total Gland, g | | | | |
| Protein | 50.8 | 53 | (+4.3) | 0.61 |
| Lipid | 763.9 | 673.2 | (−11.9) | 0.03 |
| Water | 302.6 | 338.2 | (+11.8) | 0.31 |
| Ash | 3.3 | 3.6 | (+9.1) | 0.67 |

I claim:

1. A method of increasing the milk producing capability of a female bovidae which comprises administering to the bovidae, during its mammary glands' allometric growth phase preceding first conception, an effective amount of an active agent which is 1-(4-hydroxyphenyl)-2-(1-methyl-3-(4-hydroxyphenyl)-propylamino)ethanol or a physiologically acceptable salt thereof.

2. The method of claim 1 wherein the active agent is employed as the hydrochloride salt.

3. The method of claim 2 wherein the active agent is administered during a latter portion of the allometric growth phase.

4. The method of claim 3 wherein the active agent is administered orally in a complete feed containing from 5 to 200 ppm of active agent.

5. The method of claim 4 wherein the female bovidae is a bovine and the active agent is administered during the two to four months preceding puberty.

* * * * *